United States Patent
Wilcox et al.

(10) Patent No.: US 8,195,422 B2
(45) Date of Patent: Jun. 5, 2012

(54) MEASURING THE DISTANCE BETWEEN DEVICES

(75) Inventors: Martin S. Wilcox, Redhill (GB); Adam S. Leitch, Brighton (GB)

(73) Assignee: Koninklijke Philips Electronics N.V., Eindhoven (NL)

( * ) Notice: Subject to any disclaimer, the term of this patent is extended or adjusted under 35 U.S.C. 154(b) by 1404 days.

(21) Appl. No.: 11/720,620
(22) PCT Filed: Nov. 30, 2005
(86) PCT No.: PCT/IB2005/053987
§ 371 (c)(1),
(2), (4) Date: Jun. 1, 2007
(87) PCT Pub. No.: WO2006/059296
PCT Pub. Date: Jun. 8, 2006

(65) Prior Publication Data
US 2009/0171621 A1 Jul. 2, 2009

(30) Foreign Application Priority Data
Dec. 2, 2004 (GB) .................................. 0426446.1

(51) Int. Cl.
G01P 11/00 (2006.01)
G01R 23/00 (2006.01)
G01R 35/00 (2006.01)
G01S 13/08 (2006.01)
H04B 7/00 (2006.01)

(52) U.S. Cl. .......... 702/149; 702/75; 702/106; 342/118; 455/500

(58) Field of Classification Search .................. 702/149, 702/57, 66, 75, 78, 79, 97, 106, 176; 342/118, 342/128, 129, 130, 134, 145, 146; 340/991, 340/993, 992, 988, 5.61; 455/42, 500, 502, 455/115.1–115.3, 226.1–226.3
See application file for complete search history.

(56) References Cited

U.S. PATENT DOCUMENTS

| 5,613,193 | A | 3/1997 | Ishikawa et al. |
| 7,978,049 | B2 * | 7/2011 | Leitch .......................... 340/5.72 |
| 2004/0067741 | A1 | 4/2004 | Fei et al. |
| 2005/0099333 | A1 * | 5/2005 | Gila et al. ..................... 342/118 |
| 2006/0034206 | A1 * | 2/2006 | Jacobi et al. .................. 370/324 |

FOREIGN PATENT DOCUMENTS

| EP | 1455473 A2 | 9/2004 |
| JP | EP 0940691 A2 * | 8/1999 |
| WO | WO0125060 A2 | 4/2001 |

* cited by examiner

Primary Examiner — Michael Nghiem
Assistant Examiner — Ricky Ngon (57) ABSTRACT

First and second devices having clocks which may have different clock rates. Obtaining a measure of the distance of propagation of a signal passing between the devices involves transmitting a first signal 12 from the first device to the second device. After a turnaround time TAT, a second signal 14 is transmitted from the second device to the first device. Any error in the clocks may lead to an error in the measurement of the turnaround time TAT. One device contains circuitry to calculate the ratio of the clock rates of the first and second devices, either by adjusting frequency divider ratios until there is LO frequency match, or by determining the offset frequency of an envelope of a mixed signal. The ratio of the clock rates is used to compensate the turnaround time TAT, to mitigate error. The accurate distance measurement can be used to determine if a relay attack has taken place in a vehicle security system.

18 Claims, 7 Drawing Sheets

MEASURING THE DISTANCE BETWEEN DEVICES

This invention relates to a method for obtaining a measure of the distance of propagation of a signal passing between first and second devices each having respective clocks which may have different clock rates, and in particular, although not exclusively, to a method of using the distance of propagation of a signal passing between a car and a key fob to determine if a relay attack has taken place. The invention relates also to a system comprising first and second devices having respective clocks which may have different clock rates.

It is well known for the security system of a car or other vehicle to be operated by a key fob, a key fob being a device that can enable an owner of the car to unlock the car whilst approaching it from a distance. Conventionally, the car is unlocked when the owner operates a switch of the key fob while in close proximity to the car. Key fobs that operate by means of a PKE (Passive Keyless Entry) system, in which no initiation is required by the owner, are now available. The car may become unlocked following a validation process beginning when the owner pulls on a door handle. Here, the security system must unlock the car in a very short time after the owner begins to pull on the door handle, so that the door can be opened in a single action. Alternatively, the validation process may begin when the key fob enters within a certain range of the car without the owner being required to operate a switch.

Although this provides a convenient method of the owner unlocking their car, the system can be at risk from relay attacks. A relay attack takes place when one or more transceivers intercept signals between the car and the key fob, and transmit them over longer distances than originally intended. In this way, the security system can be used to unlock the car when the owner is not close to the car and therefore does not realise that the car is being unlocked.

Figure 1:
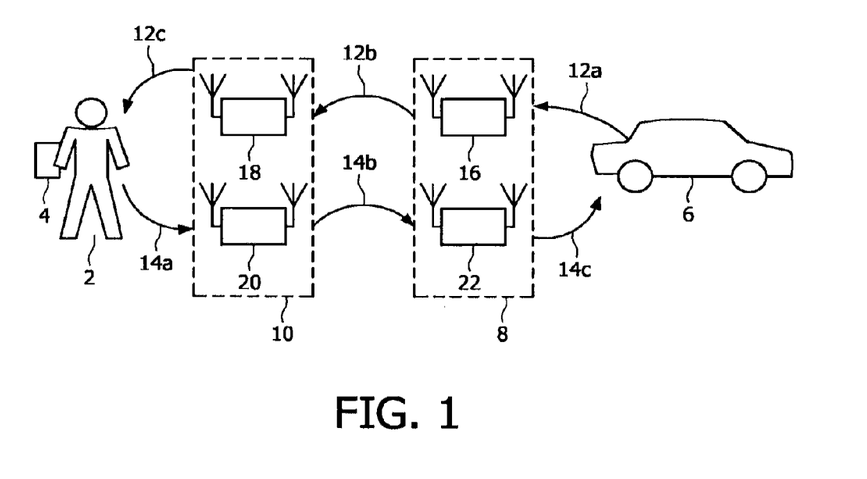
FIG. 1 illustrates schematically a relay attack on a security system of a car.

FIG. 1 shows a schematic of a relay attack, when the owner 2 carrying a key fob 4 is out of the normal range of the security system of the car 6. A first attacker 8 is positioned in close proximity to the car. A second attacker 10 is positioned between the first attacker 8 and the owner 2. The first attacker 8 can trigger the necessary function to initiate the validation process, such as pulling the door handle. The security system of the car 6 transmits a first signal 12$a$, which is intercepted by a transceiver 16 carried by the first attacker 8. The transceiver 16 copies this signal, and transmits a second signal 12$b$, derived from the first signal 12$a$, to a transceiver 18 carried by the second attacker 10. The transceiver 18 receives the second signal 12$b$ and then transmits a third signal 12$c$, derived from the second signal 12$b$, to the key fob 4 carried by the owner 2. The transceivers 16, 18 are arranged such that the first signal 12$a$ and the third signal 12$c$ are substantially identical.

The key fob 4 receives the third signal 12$c$ and responds with a proper response signal 14$a$. The second attacker 10 intercepts the response signal 14$a$ with a transceiver 20, and the transceiver 20 transmits a second response signal 14$b$ to a transceiver 22 carried by the first attacker 8. The transceiver 22 receives the second response signal 14$b$ then transmits a third response signal 14$c$ to the security system of the car 6, to unlock the car. The transceivers 20, 22 are arranged such that the first signal 12$a$ and the third signal 12$c$ are substantially identical. Since the third signal 12$c$ is generally identical to the first signal 12$a$, and the third response signal 14$c$ is generally identical to the response signal 14$a$, this attack will defeat most encryption systems.

One way of defeating a relay attack is to determine the distance the signal travels between the car and the key fob. If this distance is too large then it is inferred that the owner is not nearby and the security system will not unlock the car.

Figure 2:
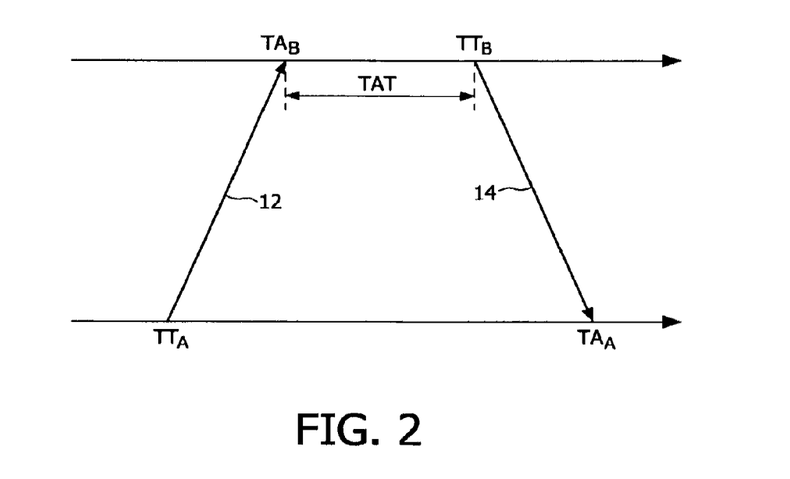
FIG. 2 illustrates the propagation of signals between two devices.

One way of finding the distance between the car and the key fob is to measure the time between transmitting a signal 12 from the car to the key fob at $TT_A$ before receiving a reply 14 at time $TA_A$, as shown in FIG. 2. The signal will be subject to a turnaround time TAT at the key fob, the turnaround time TAT being the time between receiving the signal from the car at $TA_B$ and transmitting the reply at $TT_B$. A measure of the turnaround time TAT is determined by the key fob and is transmitted to the car. By subtracting the turnaround time from the difference between $TT_A$ and $TA_A$, the propagation time of the signals 12, 14 can be determined. If the frequency of a clock within the security system and the frequency of a corresponding clock within the key fob are different, then an error may be introduced in the measurement at the key fob of the turnaround time TAT. Since the turnaround time typically will be much longer than the propagation time, the error due to the different clocks may result in a very inaccurate distance measurement. The invention is concerned with mitigating an error in the distance measurement, resulting from clock frequency errors between transceivers.

WO 2004/048997 describes obtaining the distance between two devices each having a local clock, where the two clocks can have different clock rates. This involves sending three signals between the two devices, and using timing information from the first two signals to find the ratio between the clock rate of the first device and the clock rate of the second device. The first and third signals are then used to find the time of flight, which relates directly to the distance between the two devices. A disadvantage of this system is that the time taken to exchange three messages may be unduly long, which can be problematic when validation must occur quickly, for example when the owner of the car pulls on the door handle.

WO 01/25060 describes determining the existence of a relay attack, between a key fob and a car. Instead of measuring the time of flight directly, the transmitted frequency is changed. The delay is determined from the change in frequency of the challenge signal and the change in the frequency in the response signal.

EP 1,455,473 finds the transit time between transmitting and receiving devices over a network, and synchronises the clocks on the two devices. However, the synchronisation of the clocks is not dependent on the carrier frequencies of the transmitter and receiver. Instead, the frequency of the receiving clock is varied until the minimum transit time (which is calculated in successive time intervals) remains constant. The transit time is not related to the distance between the two devices.

There are also known methods of correcting the frequency offset (which can be related to clock offset) between devices in a system, though these methods are not concerned with determining if a relay attack has taken place. US 2004/0067741 uses information about the frequency offset to change the carrier frequency of the base station so that it matches the frequency of the mobile phone. The offset information is not used to calculate the time of flight between the mobile phone and the base station. U.S. Pat. No. 5,613,193 describes measuring the frequency offset in a satellite mobile communication system. The frequency offset is present in the local oscillator of a mobile earth station, or is due to the movement of the satellite causing a Doppler shift of the signal. The frequency offset is measured in a land earth station and sent to the mobile earth station, which compensates for it by adjusting the oscillation frequency of its local oscillator. The transit time between two devices is not found or compensated for.

According to a first aspect of the invention there is provided a method of deriving a measure of the distance between first and second devices having respective clocks which may have different clock rates, the method comprising:

transmitting a first signal from the first device to the second device, the first signal having a frequency derived from the clock of the first device;

in response to receiving the first signal at the second device, transmitting a second signal from the second device to the first device, the second signal having a frequency derived from the clock of the second device;

at the second device, calculating a measure of a turnaround time at the second device relative to the clock of the second device, the turnaround time being the time between the first signal being received and the second signal being transmitted;

calculating a measure of the frequency of the clocks at the first and second devices relative to each other;

using the measure to re-calculate the turnaround time relative to the clock of the first device; and at the first device, using the re-calculated turnaround time to derive a measure of the distance between the first and second devices.

According to a second aspect of the invention there is provided a system comprising first and second devices having respective clocks which may have different clock rates:

the first device being arranged to transmit a first signal to the second device, the first signal having a frequency derived from the clock of the first device;

the second device being arranged in response to receiving the first signal to transmit a second signal to the first device, the second signal having a frequency derived from the clock of the second device;

the second device calculating a measure of a turnaround time at the second device relative to the clock of the second device, the turnaround time being the time between the first signal being received and the second signal being transmitted;

either the first or second device being arranged to calculate a measure of the frequency of the clocks at the first and second devices relative to each other;

either of the first and second devices being arranged to use the measure to re-calculate the turnaround time relative to the clock of the first device; and the first device being arranged to use the re-calculated turnaround time to derive a measure of the distance between the first and second devices.

Embodiments of the present invention will now be described, by way of example only, with reference to the accompanying drawings in which.

In the Figures, reference numerals are re-used for like elements throughout.

Figure 3:
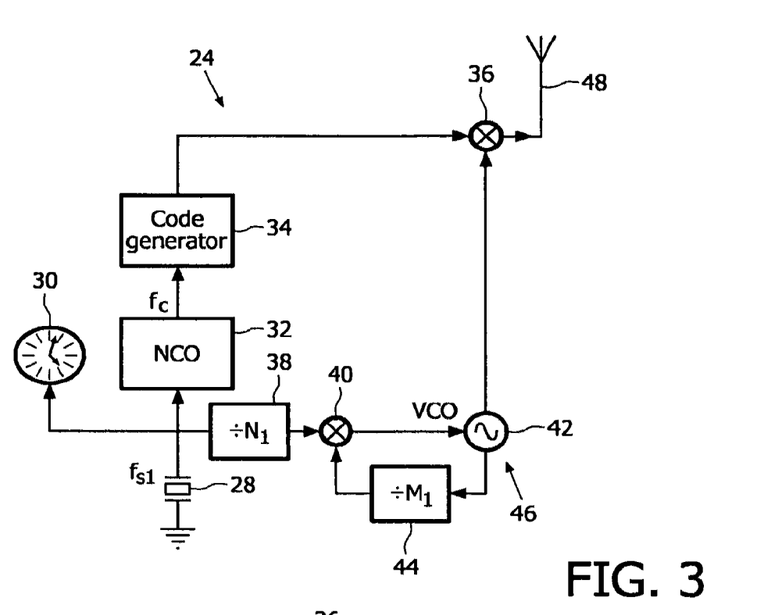
FIG. 3 is a circuit diagram of a transmitter used to illustrate the invention.
Figure 4:
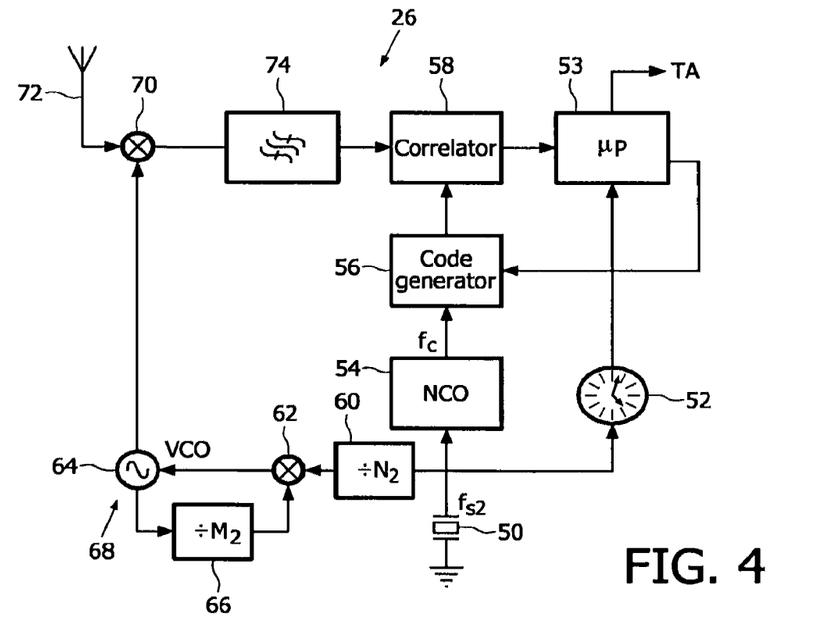
FIG. 4 is a circuit diagram of a receiver used with the FIG. 3 transmitter to illustrate the invention.

Referring firstly to FIGS. 3 and 4, a Direct-Sequence Spread Spectrum (DSSS) system comprises first and second devices 24, 26. Here, the first device is a transmitting device 24 and the second device is a receiving device 26.

The transmitting device 24 contains circuitry that includes a frequency source 28 for example, a crystal oscillator running at a frequency $f_{S1}$. The frequency source 28 is connected to a local clock 30 which derives time from the frequency source 28. The frequency source 28 is connected to an input of an NCO (Numerically Controlled Oscillator) 32. An output of the NCO 32 is connected to an input of a code generator 34. An output of the code generator 34 is connected to a first input of a mixer 36. The frequency source 28 is also connected to a first frequency divider 38 having a divider ratio of $N_1$. An output of the first frequency divider 38 is connected to a first input of a phase detector 40. An output of the phase detector 40 is connected to an input of a VCO (Voltage Controlled Oscillator) 42. An output of the VCO 42 is connected to an input of a second frequency divider 44 having a divider ratio of $M_1$. An output of the second frequency divider 44 is connected to a second input of the phase detector 40 to form a phase-locked loop (PLL) 46. A second output of the VCO 42 is connected to a second input of the mixer 36. An output of the mixer 36 is connected to an antenna 48.

The receiving device 26 contains circuitry that includes a frequency source 50, for example a crystal oscillator, running at a frequency $f_{S2}$. The frequency source 50 is connected to a local clock 52 of the device which derives time from the frequency source. The output of the local clock 52 is connected to a microprocessor 53. The frequency source 50 is connected to an input of an NCO (Numerically Controlled Oscillator) 54. An output of the NCO 54 is connected to a first input of a code generator 56. An output of the code generator 56 is connected to a first input of a correlator 58. An output of the correlator 58 is connected to a second input of the microprocessor 53. An output of the microprocessor 53 is connected to a second input of the code generator 56 to form a feedback loop. The frequency source 52 is also connected to a first frequency divider 60, which has a divider ratio of $N_2$. An output of the first frequency divider 60 is connected to the input of a phase detector 62. An output of the phase detector 62 is connected to an input of a VCO (Voltage Controlled Oscillator) 64. A first output of the VCO 64 is connected to an input of a second frequency divider 66 which has a divider ratio $M_2$. An output of the frequency divider 66 is connected to a second input of the phase detector 62 to form a phase-locked loop (PLL) 68. A second output of the VCO 64 is connected to an input of a mixer 70. An antenna 72 is connected to a second input of the mixer 70. An output of the mixer 70 is connected to an input of a bandpass filter 74. An output of the filter is connected to a second input of the correlator 58.

At the transmitting device 24, the local clock 30 counts time against the frequency source 28 running at frequency $f_{S1}$. The NCO 32 is run by the frequency source 28, and divides the frequency down to a chipping rate $f_c$. The code generator 34 generates DSSS chips at a rate of $f_c$ chips per second to produce a baseband signal, which contains data and a PRN. The PRN is known by the receiver 26. The baseband signal may include some form of encryption information, so that the car 6 can only be unlocked by the correct key fob 4. The frequency divider 38 and the PLL 46 are used to generate an RF carrier signal. The frequency divider 38 uses the frequency source 28 to generate a signal with frequency $f_{s1}/N_1$. This signal is fed into the PLL 46, which generates the RF carrier signal with a frequency $(M_1/N_1) \times f_{S_i}$. The RF carrier signal and the baseband signal are both input to the mixer 36, where the two signals are mixed to produce a modulated signal, preferably a BPSK (Binary Phase-Shift Keying) modulated signal. This signal is then transmitted to the receiving device 26 by means of the antenna 48.

The antenna 72 receives the transmitted signal and feeds it to the mixer 70. The frequency divider 60 and the PLL 68 generate a local oscillator signal. The frequency divider 60 uses the frequency source 50 to generate a signal with frequency $f_{S2}/N_2$. This signal is fed into the PLL 68, which generates the local oscillator signal with frequency $(M_2/N_2) \times f_{S2}$. The local oscillator signal should have a frequency equal or almost equal to that of the transmitted RF carrier signal. When the received BPSK signal is mixed with the local oscillator signal at the mixer 70, the baseband signal of the transmitting device is found at baseband, provided that the RF carrier signal and local oscillator signal are the same frequency. The filter 74 filters out the high frequency signal produced by the mixer 70 and any DC component so that only the baseband signal is input to the correlator. The NCO 54 is run by the frequency source 50, and divides the frequency $f_{s2}$ down to a chipping rate $f_c$. The code generator 56 generated DSSS chips at a rate of $f_c$ chips per second, to produce a replica signal that is identical to the PRN code used at the transmitting device 24. The correlator 58 correlates the replica PRN code with the received signal. Its output is detected by the microprocessor 53, the magnitude of the output of the correlator 58 is indicative of the amount of correlation between the signals. The microprocessor 53 adjusts the phase of the replica PRN code generated at the code generator 56 to produce a maximum signal from the correlator 58. Once the correct phase of the replica code is found, the time of arrival of a given point in the received signal can be determined.

Both the key fob 4 and the security system of the car 6 contain a transmitting device 24 and a receiving device 26. The transmitting device 24 and the receiving device 26 on the car 6 use the same frequency source 28, 50 with frequency $f_{SA}$, to run the same clock 30, 52. The transmitting device 24 and the receiving device 26 on the car 6 use the same divider ratios: $N_A$ for the first frequency divider 38, 64; and $M_A$ for the second frequency divider 44, 60. The transmitting device 24 and the receiving device 26 on the key fob 4 use the same frequency source 28, 50 with frequency $f_{SB}$, to run the same clock 30, 52. The transmitting device 24 and the receiving device 26 on the key fob 4 use the same divider ratios: $N_B$ for the first frequency divider 38, 64; and $M_B$ for the second frequency divider 44, 60.

Referring again to FIG. 2, operation of the devices will now be described. The security system of the car 6 transmits a first signal 12 including a reference point at time $TT_A$ using its transmitting device 24. The security system of the car 6 stores a record of this time $TT_A$. The key fob 4 receives the first signal 12, and uses its correlator 58 to correlate the received signal with the replica code to find the time of arrival $TA_B$ of the reference point. After a turnaround time TAT, the key fob 4 uses its transmitting device 24 to send a second signal 14 back to the security system of the car 6 having a reference point at time $TT_B$. The baseband signal of the second signal 14 contains data identifying either the time of arrival of the first signal at the key fob 4, $TA_B$ and the time of transmission of the second signal from the key fob 4, $TT_B$ or the turnaround time TAT. The car receives the second signal 14, and correlates the received signal with the replica code to find the time of arrival $TA_A$. The time-of-flight (ToF) is calculated at the security system of the car 6 and is given by:

$$ToF = \frac{1}{2}[(TT_A - TA_A) - (TA_B - TT_B)] \qquad \text{Equation (1)}$$

Here it is assumed that there is no error in the local clock 30, 52 of either device, so the times are measured against absolute time.

Figure 5:
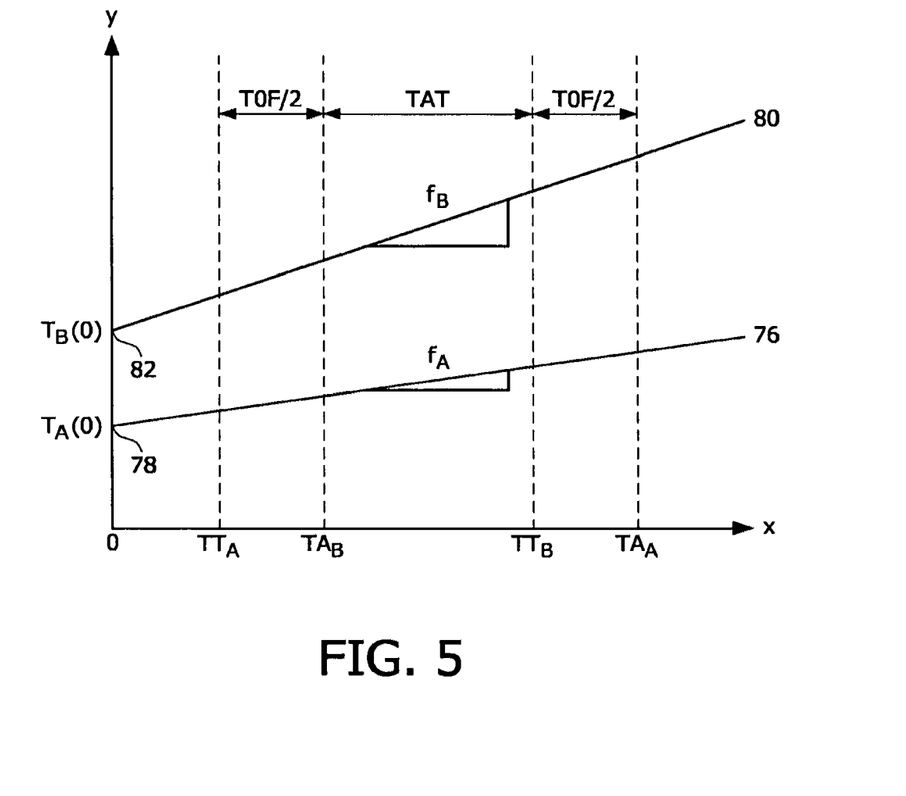
FIG. 5 is a graph displaying the clock errors of the FIGS. 3 and 4 devices.

FIG. 5 is a graph of the time recorded by the clock at Unit A (e.g. the security system of the car 6) or Unit B (e.g. the key fob 4) on the y-axis against absolute time on the x-axis. Line 76 shows the time recorded by the security system of the car 6 against absolute time. An intercept 78 of a line 76 with the y-axis gives the clock offset $T_A(0)$. The gradient of the line 76 gives the clock rate of the security system of the car 6, $f_A$ i.e. how many seconds the local clock 30, 52 of the car 6 records in one second of absolute time. A second line 80 shows the time recorded by the key fob 4 against absolute time. An intercept 82 of the second line 80 with the y-axis gives the clock offset $T_B(0)$. The gradient of the second line 80 gives the clock rate of the key fob 4, $f_B$ i.e. how many seconds the local clock 30, 52 of the key fob 4 records in one second of absolute time. If there is no clock error in the local clock 30, 52 of the key fob 4 and security system of the car 6 then $f_A = f_B = 1$ and $T_A(0) = T_B(0) = 0$, and the expression in equation (1) for the time-of-flight ToF is that measured by the security system of the car 6.

If a clock error is present in both local clocks 30, 52, then the time-of-flight ToF calculated by the security system of the car 6 is no longer correct. If no correction is made for the error in the local clocks 30, 52 then the time-of-flight ToF calculated by the car is:

$$ToF = \frac{1}{2}[(TT_A - TA_A) \times f_A - (TA_B - TT_B) \times f_B] \qquad \text{Equation (2)}$$

The clock offset of each of the local clocks 30, 52 cancels out in this two-way method.

It is mathematically impossible to find the value of $f_A$ and $f_B$ independently. Therefore, an exact measure of the time-of-flight ToF cannot be calculated. However, the inventors have determined that it is possible to obtain a measure of $f_B/f_A$, the clock rate of the key fob 4 divided by the clock rate of the car 6.

It is preferable that the majority of the computation carried out is performed at the security system of the car 6. This is because the car 6 has the benefit of a large battery and protection against temperature variation, and because it typically has more volume available than at the key fob 4. However, some of the computation can be carried out at the key fob 4. If the amount of electronics in the key fob is kept to a minimum, the key fob can be slim and can be kept in the owner's wallet without being particularly obtrusive.

Two alternative methods can be used to obtain a measure of $f_B/f_A$. Each of these methods involves adapting the circuitry of the receiving device 26 at either the security system of the car 6 or the key fob 4.

Figure 6:
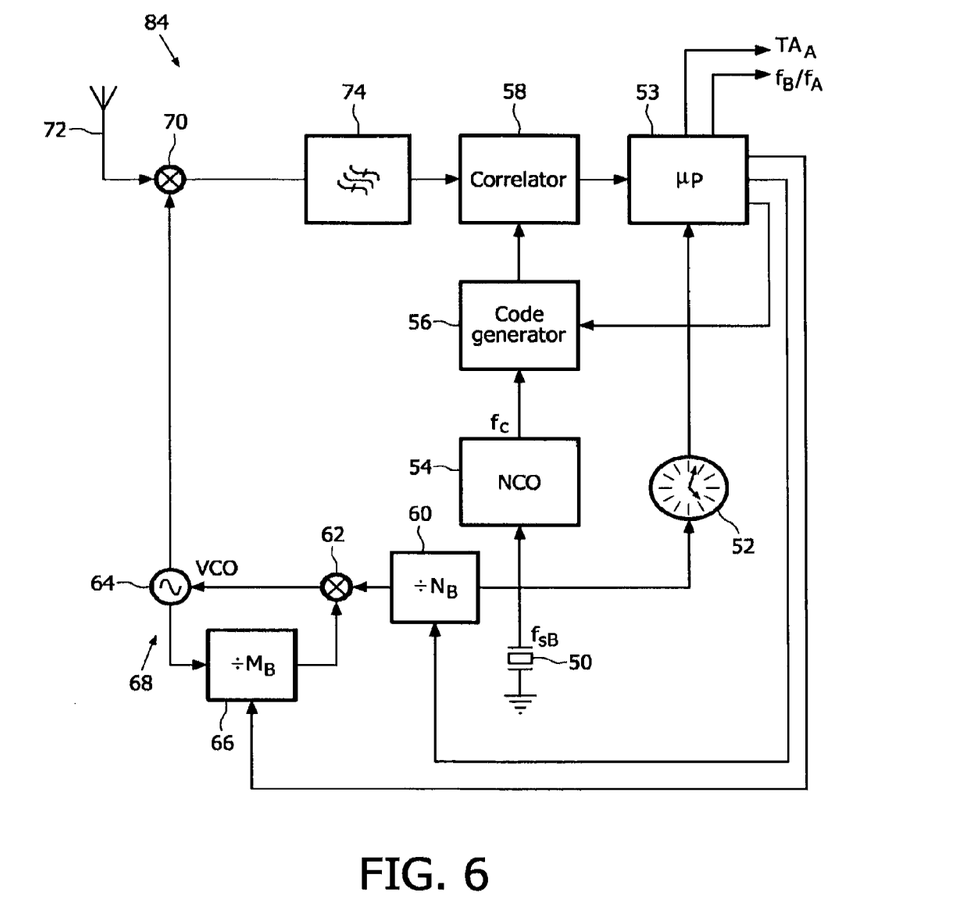
FIG. 6 is a circuit diagram of a receiver operable to match a local oscillator frequency to the frequency of a received signal according to an embodiment of the invention.

FIG. 6 shows the circuitry of a receiving device 84 for calculating $f_B/f_A$ at the security system of the car 6. This is based on the receiving device 26. Additional outputs of the microprocessor 53 are connected to control inputs of the first frequency divider 60 and the second frequency divider 66, thereby producing feedback loops.

The security system of the car 6 and the key fob 4 are manufactured so that the carrier frequencies of the two devices are nearly identical. However, with time the frequencies of the frequency sources 28, 50, and thus also the local clocks 30, 52, of the devices can drift so that the carrier frequencies of the two devices 6, 4 are no longer equal. If the local oscillator signal produced at the receiving device 84 does not have the same frequency as the RF carrier signal on the incoming signal, when these two signals are mixed at the mixer 70 the baseband signal will not be centred at zero Hertz. In this case, the correlator 58 does not produce as large an output as when the carrier frequency is matched. The maximum correlation occurs when the RF carrier signal has the same frequency as the local oscillator signal and the PRN codes are phase aligned. The microprocessor 53 varies the divider ratios $M_B$ and $N_B$ to maximise the output signal from the correlator, once the correct phase of the replica PRN code has been established as described above.

At some previous time, before the clocks have drifted, the frequency of the local oscillator and the frequency of the RF carrier are identical. This gives the expression:

$$\frac{f_{S_A} M_A}{N_A} = f_{carrier} = \frac{f_{S_B} M_B}{N_B} \qquad \text{Equation (3)}$$

This step usually occurs when the car and the key fob are manufactured, though it can take place any time previous to the first signal being transmitted. The car keeps a record of the divider ratios $M_A$, $N_A$, $M_B$ and $N_B$, and the carrier frequency when this result is true. At some later time, when the clocks have drifted to values $f_{S_A}'$ and $f_{S_B}'$, the two frequencies may no longer be matched. The receiving device 84 on the security system of the car 6 adjusts the divider ratios $M_A$ and $N_A$ to new values $M_A'$ and $N_A'$ to match the frequency of the local oscillator in the security system of the car 6 to the frequency of the RF carrier transmitted by the key fob 4, when the second signal is received. The divider ratios $M_B$, $N_B$ on the key fob 4 are not changed. The new carrier frequency is given by:

$$\frac{f_{S_A}' M_A'}{N_A'} = f_{carrier}' = \frac{f_{S_B}' M_B}{N_B} \qquad \text{Equation (4)}$$

Dividing equation 4 by equation 3 yields the result:

$$\frac{f_{S_B}'/f_{S_B}}{f_{S_A}'/f_{S_A}} = \frac{M_A' N_A}{N_A' M_A} \qquad \text{Equation (5)}$$

The clock rates $f_A$ and $f_B$ are given by $f_A = f_{S_A}'/f_{S_A}$ and $f_B = f_{S_B}'/f_{S_B}$. This therefore leads to a result for $f_B/f_A$:

$$\frac{f_B}{f_A} = \frac{M_A' N_A}{N_A' M_A} \qquad \text{Equation (6)}$$

That is, the clock rate of the key fob 4 divided by the clock rate of the security system of the car 6 are calculated by matching the frequency of the signals of the two devices, since the divider ratios used when the two frequencies were initially matched are known.

In this case, when the first signal 12 is sent from the security signal of the car 6 to the key fob 4, no alterations are made to any of the divider ratios $M_A$, $N_A$, $M_B$ and $N_B$. After a turnaround time TAT, the key fob 4 transmits the second signal 14 to the car 6. This contains either the individual values of $TA_B$ and $TT_B$ or a composite value ($TT_B - TA_B$). When the second signal 14 is received at the security system of the car 6, the receiving device 84 adjusts the divider ratios $M_A$ and $N_A$, and calculates $f_B/f_A$ using these adjusted divider ratios.

Once $f_B/f_A$ has been found, and is known at the security system of the car 6, it is used to compensate the turnaround time TAT measured at the key fob 4. An improved estimate of the time-of-flight ToF is:

$$ToF = \frac{1}{2}\left\{ f_A(ToA_2 - ToT_1) - \frac{f_B(ToT_2 - ToA_1)}{f_B/f_A} \right\} \qquad \text{Equation (7)}$$

$$= \frac{1}{2} f_A\{(ToA_2 - ToT_1) - (ToT_2 - ToA_1)\}$$

This calculation is always carried out at the security system of the car. There is an error in this measurement if the clock rate $f_A$ of the car 6 is not equal to one. However it is likely that the error in the local clock 30, 52 of the security system of the car 6 will be smaller than the error in the local clock 30, 52 of the key fob, since the physical conditions are likely to be more stable in the car 6. The distance between the car 6 and the key fob 4 is found by multiplying the time-of-flight ToF by the speed of light.

In an alternative embodiment, more of the calculations are carried out at the key fob 4. In this embodiment, the adapted receiving device 84 is present in the key fob 4, and the original receiving device 26 is present in the security system of the car 6. When the first signal 12 is received from the security system of the car 6 at the key fob 4, the receiving device 84 adjusts the divider ratios $M_B$ and $N_B$, and calculates $f_B/f_A$ using these adjusted divider ratios. After a turnaround time TAT, the key fob 4 transmits the second signal 14 to the car. The signal contains either the individual values of $TA_B$, $TT_B$, and $f_B/f_A$ or a composite value of the compensated turnaround time TAT, $(TT_B - TA_B)/(f_B/f_A)$. When the second signal 14 is received at the security system of the car 6, no alterations are made to any of the divider ratios $M_A$, $N_A$, $M_B$ and $N_B$ therein. The time-of-flight ToF is calculated at the car 6 using equation 7.

Figure 7:
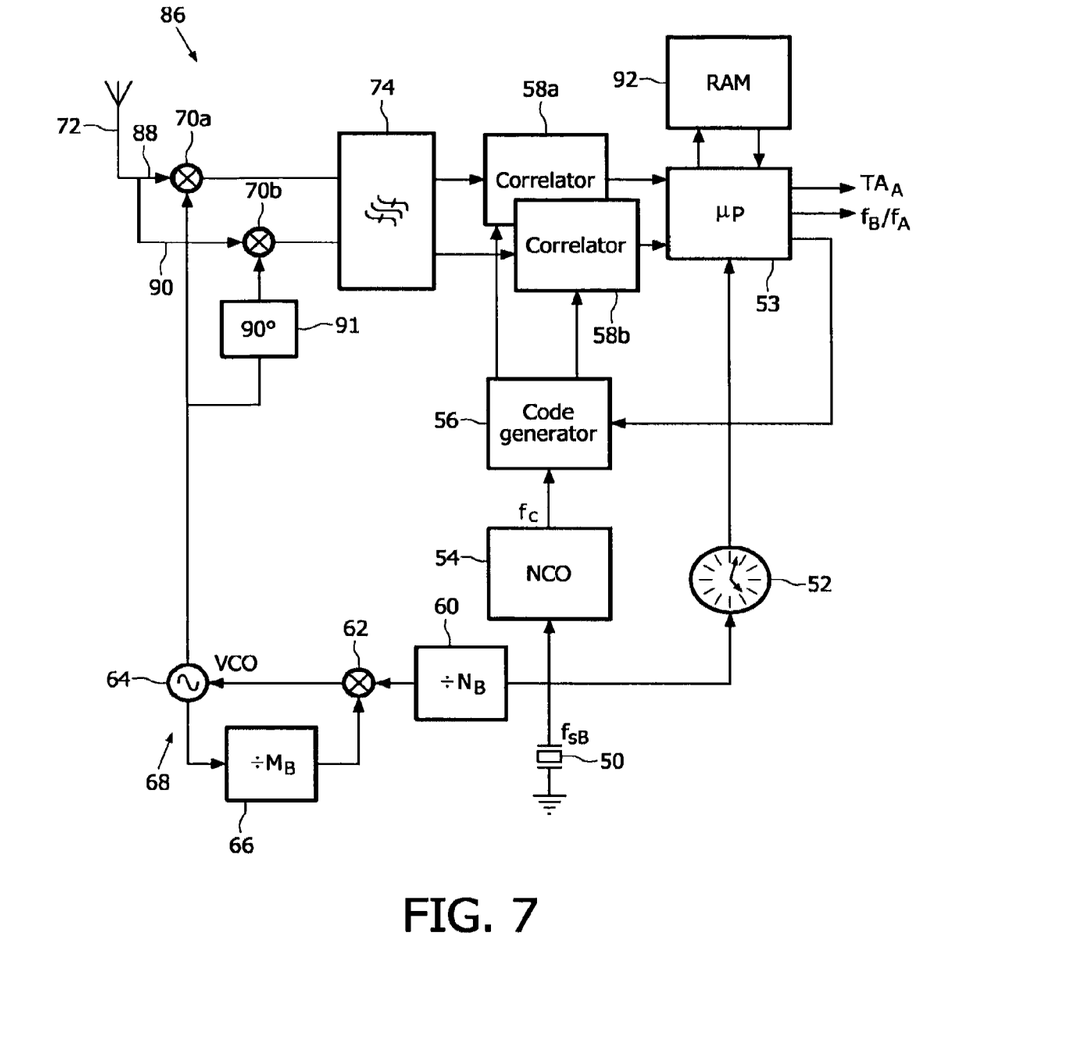
FIG. 7 is a circuit diagram of a receiver to calculate the difference between the local oscillator frequency and the frequency of the received signal according to an embodiment of the invention.

FIG. 7 shows the circuitry of a further receiving device 86 for calculating $f_B/f_A$ at the security system of the car 6. This is based on the receiving device 26. A received signal is split onto two channels, an I channel 88 and a Q channel 90. Each channel 88, 90 connects to a respective input of a mixer 70a, 70b. The second output of the VCO 64 is split into two channels, where one channel is phase shifted by $\pi/2$ by a phase shifter 91. The other channel connects to the mixer 70a on the I channel 88. The channel with a $\pi/2$ phase shift connects to the mixer 70b on the Q channel 90. The output of each mixer 70a, 70b connects to a respective input of a dual channel filter 74. The output of the filter 74 on the I channel 88 connects to the input of a correlator 58a. The output of the filter 74 on the Q channel 90 connects to the input of a correlator 58b. The code generator 56 has two outputs, where one output connects to the input of a respective correlator 58a, 58b. The output of each correlator 58a, 58b connects to the microprocessor 53. An additional output of the microprocessor 53 connects to the input of a memory module 92. An output of the memory module 92 connects to a further input of the microprocessor 53.

At the mixers 70a, 70b the local oscillator signal from the VCO 64 is mixed with the incoming signal, to down-convert the incoming signal to baseband. If the local oscillator signal is exactly in phase with the RF carrier signal on the I channel 88, then all the data is output at the mixer 70a on the I channel. If the local oscillator signal is exactly in phase with the RF carrier signal on the Q channel 90, then all the data is output at the mixer 70b on the Q channel 90. If the local oscillator signal is not exactly in phase with the RF carrier signal on either the I channel 88 or the Q channel 90, the energy is split between the I channel 88 and the Q channel 90. However, if the local oscillator signal has a different frequency to the RF carrier signal, the local oscillator signal will not have a constant phase relationship with either the I channel 88 or the Q channel 90, and the amount of energy on each channel varies with time. Because BPSK modulation is used, both channels contain the same information.

Figure 8:
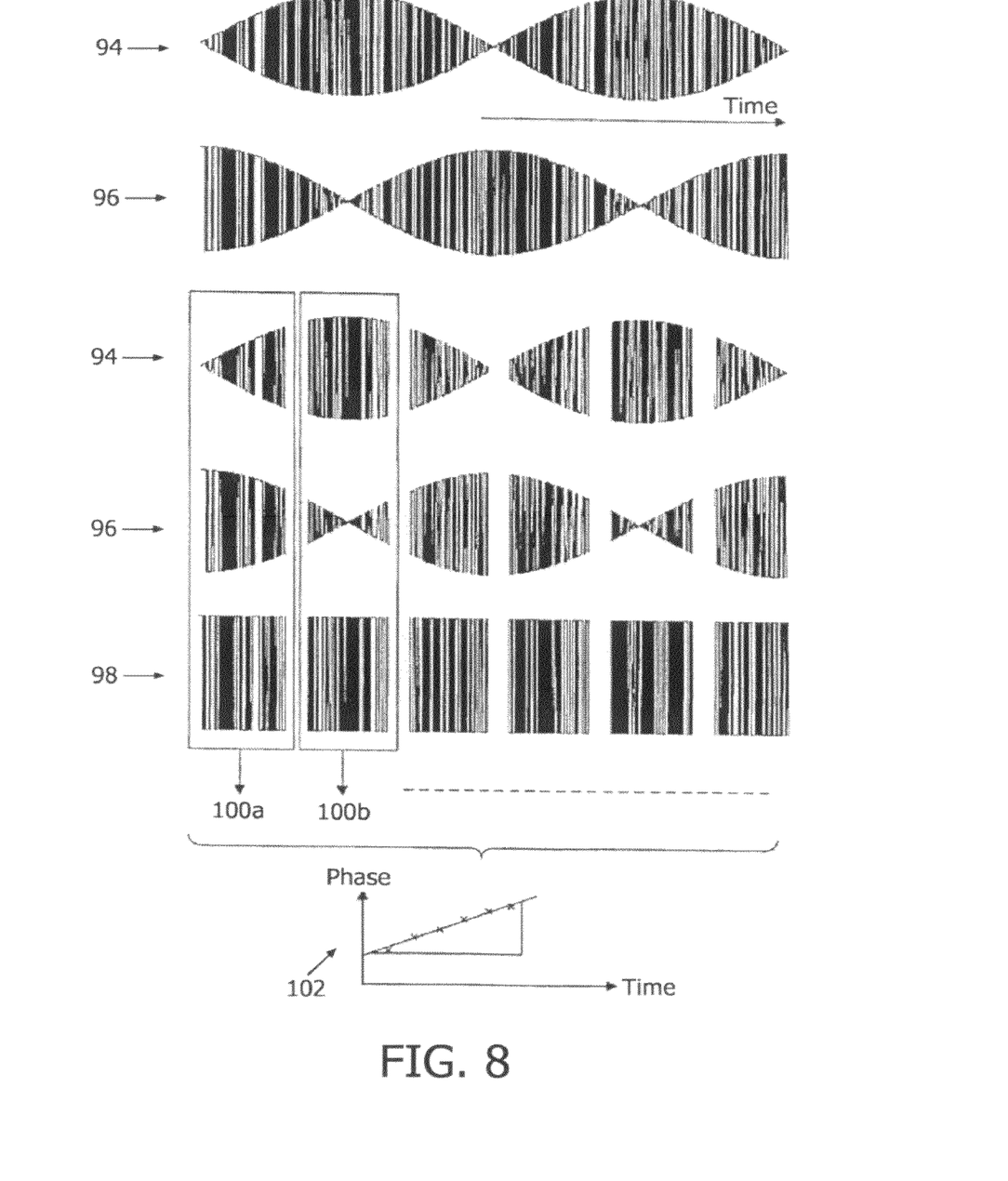
FIG. 8 shows how the data on I and Q channels can be used to produce a plot of phase with time according to an embodiment of the invention.

This effect is shown in FIG. 8. Graph 94 shows the data on the I channel 88 that is output from the mixer 70a and passed through the filter 74. Graph 96 shows the data on the Q channel 90 that is output from the mixer 70b and passed through the filter 74. The effect is that the data in each signal 94, 96 is contained within a sinusoidal envelope, with the envelope of the I channel 88 being out of phase by $\pi/2$ with the envelope of the Q channel 90. As can be seen from the Figure, the same BPSK data is present on each channel 88, 90. The frequency of the envelope function is $f_{offset}$, the offset frequency, where $f_{offset}$ is the difference in frequency between the transmitted RF carrier signal and the locally generated local oscillator signal.

A value for the frequency offset is determined from the frequency of the envelope function. One way to do this is simply to take arctan(I/Q) at a series of points. This gives a plot of the phase as a function of time, and the gradient of the straight line produced gives $f_{offset}$. In practice, it is more accurate first to correlate the data in the I channel 90 with replica code generated in the code generator 56 using the correlator 58a, and to correlate the data in the Q channel 88 with replica code generated in the code generator 56 using the correlator 58b. This prevents the modulated data from affecting the results, and reduces the effect of noise on the output. The correlators 58a, 58b are first used with the microprocessor 53 in a feedback loop to generate the replica code at the correct code phase, which also yields the value of $TA_A$, as described above.

The I channel data 94, Q channel data 96 and the replica code at the correct code phase 98 are split into small duration portions 100a, 100b etc. The correlators 58a, 58b divide out the modulation of the data on the I and Q channels 94, 96 to extract a point on the envelope signal of the I channel 94 and the Q channel 96. The microprocessor 53 then performs the arctan(I/Q) function to calculate the phase. The phase value is stored in the memory module 92, and correlations are repeated. The memory module 92 then sends all the data values back to the microprocessor 53. These data values are used by the microprocessor 53 to create a plot of phase against time, where the gradient is equal to $f_{offset}$. The correlation period should be shorter than the reciprocal of the frequency offset, to prevent the correlation from distorting the results.

The frequency offset is related to the ratio of the clock rate $f_B$ of the key fob 4 and the clock rate $f_A$ of the security system of the car. The frequency offset is given by:

$$f_{offset} = f'_{localoscillator} - f'_{carrier} \quad \text{Equation (8)}$$

$$= f'_{S_A} \frac{M_A}{N_A} - f'_{S_B} \frac{M_B}{N_B}$$

where $f'_{carrier}$ and $f'_{localoscillator}$ are the RF carrier frequency and local oscillator frequency when the local clocks 30, 52 have drifted to frequencies $f'_{S_A}$ and $f'_{S_B}$ respectively. The divider ratios $M_A$, $N_A$ on the car 4 and the divider ratios $M_B$, $N_B$ on the key fob 6 keep their original values. Using equation 3, this can be re-written as:

$$f_{offset} = f'_{S_A} \frac{f_{carrier}}{f_{S_A}} - f'_{S_B} \frac{f_{carrier}}{f_{S_B}} \quad \text{Equation (9)}$$

$$= \frac{f'_{S_A}}{f_{S_A}} f_{carrier} \left\{ 1 - \frac{f'_{S_B} / f_{S_B}}{f'_{S_A} / f_{S_A}} \right\}$$

$$= \frac{f'_{S_A}}{f_{S_A}} f_{carrier} \{1 - f_B / f_A\}$$

If it is assumed that the clock in the car has not drifted, then $f'_{S_A}/f_{S_A} \approx 1$, the ratio of the clock rate of the car $f_A$ with the clock rate of the key fob $f_B$ can be found:

$$f_B / f_A \approx 1 - \frac{f_{offset}}{f_{carrier}} \quad \text{Equation (10)}$$

The microprocessor 53 performs the above calculation using the result for $f_{carrier}$, the RF carrier frequency when both local clocks 30, 52 have the same clock rate, already known from an earlier time (such as when the components of the system are manufactured).

In this case, when the first signal 12 is sent from the security signal of the car 6 to the key fob 4, no measurement is made of the offset frequency. After a turnaround time TAT, the key fob 4 transmits the second signal 14 to the car, where the signal contains either the individual values of $TA_B$ and $TT_B$ or a composite value ($TT_B$–$TA_B$). When the second signal is received at the security system of the car 6, the receiving device 84 measures the offset frequency and calculates $f_B/f_A$ using the offset frequency. The time-of-flight ToF is calculated at the car 6 using equation 7.

Alternatively, more of the calculations can be carried out at the key fob 4. Here, the receiving device 86 is present on the key fob 4, and the original receiving device 26 is present on the security system of the car 6. When the first signal 12 is sent from the security system of the car 6 to the key fob 4, the receiving device 84 makes a measurement of the offset frequency, and uses it to calculate $f_B/f_A$. After a turnaround time TAT, the key fob 4 transmits the second signal 14 to the car, which contains either the individual values of $TA_B$, $TT_B$, and $f_B/f_A$ or a composite value of the compensated turnaround time TAT, ($TT_B$–$TA_B$)/($f_B/f_A$). When the second signal is received at the security system of the car 6, no measurement of the offset frequency is made. The time-of-flight ToF is calculated at the car 6 using equation 7.

Figure 9A:
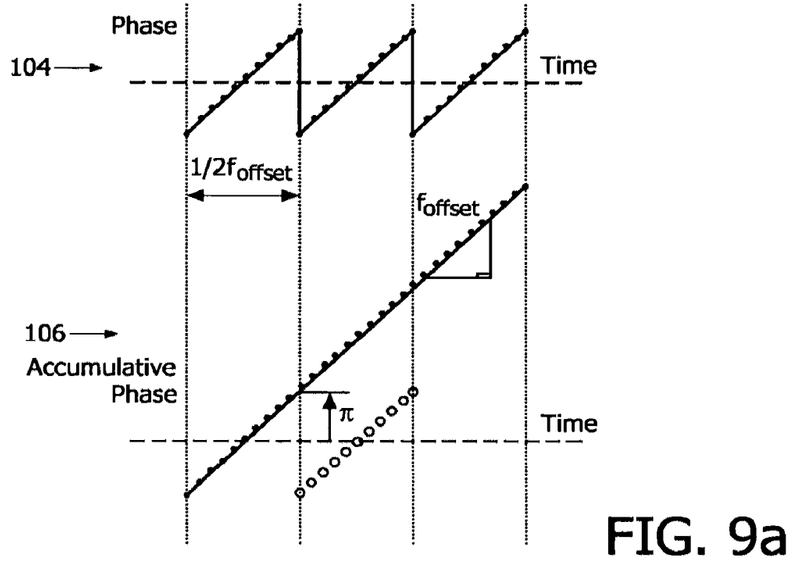
FIG. 9a is a plot of phase against time derived from the FIG. 8 data when there are several data points in each interval of $\pi$.
Figure 9B:
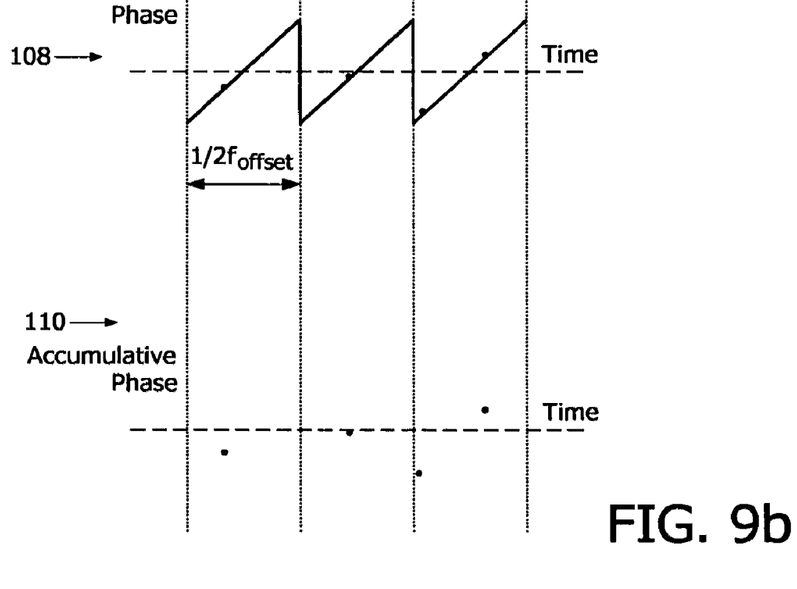
FIG. 9b is a plot of phase against time derived from the FIG. 8 data when there are few data points in each interval of $\pi$.

The arctan function only produces results in the interval $-\pi/2 \leq x \leq \pi/2$ in phase, causing discontinuities to occur every half wavelength of the offset frequency, as shown in FIGS. 9a and 9b. Measuring the gradient over a discontinuity causes an error. In FIG. 9a, many correlations are performed in each interval of $-\pi/2 \leq x \leq \pi/2$ in phase as shown in graph 104. It is relatively straightforward for the receiver 86 to identify the discontinuities in this case. A plot of accumulative phase against time is produced by shifting up the phase in each successive interval by π, as shown in graph 106. The graph of accumulative phase against time 106 can be used to find the true gradient. However, generating so many measurements of the phase in a given time interval may require a large amount of processing resources. FIG. 9b shows a graph when fewer measurements of phase are carried out in each interval of time. It is more difficult for the receiving device 86 to identify the discontinuities in this case, and a graph of accumulative phase against time 110 cannot be calculated unless the system already has an idea of the frequency offset.

This problem is solved if a combination of the two methods to find $f_B/f_A$ is used. First, $N_A$ and $M_A$ are tuned to reduce the frequency offset. Since the size of the interval between discontinuities shown in graphs 104, 106, 108 and 110 is related to the inverse of the frequency offset, this increases the size of interval between discontinuities. There are, therefore, more correlations in each interval of $-\pi/2 \leq x \leq \pi/2$ of the phase, so the graph of accumulative phase against time is easily generated.

The invention is not limited to car security systems, but instead has broader applications. In another embodiment of the invention (not shown), the system is used to create a positioning system. This is used for example to track equipment, patients and doctors in a hospital. There is an infrastructure of base stations, which contain similar circuitry to that in the car 6. The equipment, patients and doctors each carry a tag containing similar circuitry to that in the key fob 4. The base stations run independently from their own clocks, so no cables are needed between them as in previous systems. Each time a tag needs to be located there is two-way communication between the tag and at least three of the base stations. The base-stations compensate the turnaround time at the tags to arrive at an accurate measure of the distance of the tag from each base station, and therefore are able to calculate the position of the tag.

Although the present invention has been described with respect to the above embodiments, it should be apparent to those skilled in the art that modifications can be made without departing from the scope of the invention.

The invention claimed is:

1. A method of deriving a measure of the distance between first and second devices having respective clocks which may have different clock rates, the method comprising the act of:
   transmitting a first signal from the first device to the second device, the first signal having a frequency derived from the clock of the first device;
   in response to receiving the first signal at the second device, transmitting a second signal from the second device to the first device, the second signal having a frequency derived from the clock of the second device;
   at the second device, calculating a measure of a turnaround time at the second device relative to the clock of the second device, the turnaround time being a time between the first signal being received and the second signal being transmitted;
   calculating a frequency measure of the frequency of the at the first and second devices relative to each other, wherein the frequency measure comprises a measure of a ratio of the clock frequencies;
   using the frequency measure to re-calculate the turnaround time relative to the clock of the first device; and
   at the first device, using the re-calculated turnaround time to derive a measure of the distance between the first and second devices.

2. The method as claimed in claim 1, wherein the frequency measure calculating act is performed at the second device, the method further comprising communicating the frequency measure to the first device.

3. The method as claimed in claim 1, wherein the frequency measure calculating act is performed at the first device.

4. A method of deriving a measure of the distance between first and second devices having respective clocks which may have different clock rates, the method comprising the act of:
   transmitting a first signal from the first device to the second device, the first signal having a frequency derived from the clock of the first device;
   in response to receiving the first signal at the second device, transmitting a second signal from the second device to the first device, the second signal having a frequency derived from the clock of the second device;
   at the second device, calculating a measure of a turnaround time at the second device relative to the clock of the second device, the turnaround time being a time between the first signal being received and the second signal being transmitted;
   calculating a frequency measure of the frequency of the clocks at the first and second devices relative to each other;
   using the frequency measure to re-calculate the turnaround time relative to the clock of the first device; and
   at the first device, using the re-calculated turnaround time to derive a measure of the distance between the first and second devices,
   wherein at least one device of the first and second devices has at least one frequency divider which is used to derive a local oscillator signal from the clock of the at least one device, the method further comprising determining a divider ratio of each of the at least one frequency divider which gives rise to substantially equal frequency local oscillator signals in the first and second devices at a time prior to transmission of the first signal; and storing the divider ratio of each frequency divider in either the first device or the second device.

5. The method as claimed in claim 4, wherein the frequency measure calculating act comprises the acts of:
   varying the divider ratio of the at least one frequency divider until it provides the local oscillator signal which is substantially equal to a carrier of either the first signal or the second signal, whichever is being received at the at least one device at which the divider ratio is varied.

6. A method of deriving a measure of the distance between first and second devices having respective clocks which may have different clock rates, the method comprising the act of:
   transmitting a first signal from the first device to the second device, the first signal having a frequency derived from the clock of the first device;
   in response to receiving the first signal at the second device, transmitting a second signal from the second device to the first device, the second signal having a frequency derived from the clock of the second device;
   at the second device, calculating a measure of a turnaround time at the second device relative to the clock of the second device, the turnaround time being a time between the first signal being received and the second signal being transmitted;
   calculating a frequency measure of the frequency of the clocks at the first and second devices relative to each other;
   using the frequency measure to re-calculate the turnaround time relative to the clock of the first device; and at the first device, using the re-calculated turnaround time to derive a measure of the distance between the first and second devices, wherein the frequency measure calculating act comprises the acts of:

mixing the first signal or the second signal, whichever is received at a receiving device being one of the first device or the second device, with a local oscillator signal of the receiving device to form a mixed signal; and determining frequency of an envelope of the mixed signal.

7. The method as claimed in claim 6, further comprising, prior to the mixing and determining acts, the act of reducing a frequency offset by adjusting a divider ratio of at least one divider in the receiving device.

8. The method as claimed in claim 6, wherein the frequency measure calculating act comprises the acts of:

successively calculating arctan of a ratio of an in-phase mixed signal to a quadrature mixed signal at spaced intervals; and determining a gradient of a line provided by results of the act of successively calculating the arctan.

9. A system comprising:

a first device; and a second device, the first and second devices having respective clocks which may have different clock rates, the first device being arranged to transmit a first signal to the second device, the first signal having a frequency derived from the clock of the first device;

the second device being configured, in response to receiving the first signal, to transmit a second signal to the first device, the second signal having a frequency derived from the clock of the second device;

the second device calculating a measure of a turnaround time at the second device relative to the clock of the second device, the turnaround time being a time between the first signal being received and the second signal being transmitted;

either the first device or the second device being configured to calculate a frequency measure of a frequency of the clocks at the first and second devices relative to each other, wherein the frequency measure comprises a measure of a ratio of the clock frequencies;

either of the first device and the second device being configured to use the frequency measure to re-calculate the turnaround time relative to the clock of the first device; and the first device being configured to use the re-calculated turnaround time to derive a measure of the distance between the first and second devices.

10. The system as claimed in claim 9, wherein the second device is configured to calculate the frequency measure, and to communicate the frequency measure to the first device.

11. The system as claimed in claim 9, wherein the first device is configured to calculate the frequency measure.

12. The system as claimed in claim 9, wherein the first device forms part of a vehicle security system, and the second device forms part of a vehicle access transceiver.

13. The system as claimed in claim 9, being a positioning system comprising plural first devices each constituting a base station and at least one second device being a mobile device.

14. A system comprising:

a first device; and a second device, the first and second devices having respective clocks which may have different clock rates, the first device being arranged to transmit a first signal to the second device, the first signal having a frequency derived from the clock of the first device;

the second device being configured, in response to receiving the first signal, to transmit a second signal to the first device, the second signal having a frequency derived from the clock of the second device;

the second device calculating a measure of a turnaround time at the second device relative to the clock of the second device, the turnaround time being a time between the first signal being received and the second signal being transmitted;

either the first device or the second device being configured to calculate a frequency measure of a frequency of the clocks at the first and second devices relative to each other;

either of the first device and the second device being configured to use the frequency measure to re-calculate the turnaround time relative to the clock of the first device; and the first device being configured to use the re-calculated turnaround time to derive a measure of the distance between the first and second devices, wherein a one device of the first and second devices has at least one frequency divider which is used to derive a local oscillator signal from the clock of the at least one device, the system being configured to determine a divider ratio of each frequency divider which gives rise to substantially equal frequency local oscillator signals in the first and second devices at a time prior to transmission of the first signal, and at least one of the first and second devices being configured to store the divider ratio.

15. The system as claimed in claim 14, wherein the one device is configured to calculate the frequency measure is further configured to:

vary the divider ratio of the at least one frequency divider until it provides the local oscillator signal which is substantially equal to a carrier of either the first signal or the second signal, whichever is being received at the one device.

16. A system comprising:

a first device; and a second device, the first and second devices having respective clocks which may have different clock rates, the first device being arranged to transmit a first signal to the second device, the first signal having a frequency derived from the clock of the first device;

the second device being configured, in response to receiving the first signal, to transmit a second signal to the first device, the second signal having a frequency derived from the clock of the second device;

the second device calculating a measure of a turnaround time at the second device relative to the clock of the second device, the turnaround time being a time between the first signal being received and the second signal being transmitted;

either the first device or the second device being configured to calculate a frequency measure of a frequency of the clocks at the first and second devices relative to each other;

either of the first device and the second device being configured to use the frequency measure to re-calculate the turnaround time relative to the clock of the first device; and the first device being configured to use the re-calculated turnaround time to derive a measure of the distance between the first and second devices, wherein a one device of the first or second devices which is configured to calculate the frequency measure is further configured to mix the first signal or the second signal, whichever is received at the one device, with the local oscillator signal of the one device for forming a mixed signal, and to determine the frequency of an envelope of the mixed signal.

17. The system as claimed in claim 16, wherein the one device is configured to reduce a frequency offset by adjusting a divider ratio of at least one divider in the one device prior to determining the frequency of an envelope of the mixed signal.

18. The system as claimed in claim 16, wherein the one device is further configured to perform successive arctan calculations of a ratio of an in-phase mixed signal to a quadrature mixed signal at spaced intervals, and to determine a gradient of a line provided by results of successive arctan calculations.

* * * * *